US008389700B2

(12) United States Patent
Langrana et al.

(10) Patent No.: US 8,389,700 B2
(45) Date of Patent: *Mar. 5, 2013

(54) AGENT DELIVERY SYSTEM CAPABLE OF SELECTIVELY RELEASING AN AGENT

(75) Inventors: Noshir A. Langrana, West Windsor, NJ (US); David C. Lin, East Windsor, NJ (US); Bernard Yurke, Plainfield, NJ (US)

(73) Assignees: Alcatel Lucent, Paris (FR); Rutgers, The State University of New Jersey, New Brunswick, NJ (US)

( * ) Notice: Subject to any disclaimer, the term of this patent is extended or adjusted under 35 U.S.C. 154(b) by 719 days.

This patent is subject to a terminal disclaimer.

(21) Appl. No.: 10/260,243

(22) Filed: Sep. 30, 2002

(65) Prior Publication Data

US 2004/0062808 A1   Apr. 1, 2004

Related U.S. Application Data

(63) Continuation-in-part of application No. 10/252,287, filed on Sep. 23, 2002, now Pat. No. 7,919,600.

(51) Int. Cl.
*C07H 21/02* (2006.01)
*C12Q 1/68* (2006.01)
(52) U.S. Cl. ............................. 536/23.1; 435/6.12
(58) Field of Classification Search .............. 514/772.4; 424/401; 536/23.1; 435/6, 6.12
See application file for complete search history.

(56) References Cited

U.S. PATENT DOCUMENTS

| | | | |
|---|---|---|---|
| 5,175,270 A | 12/1992 | Nilsen et al. | |
| 5,736,316 A | 4/1998 | Irvine et al. | |
| 5,770,358 A * | 6/1998 | Dower et al. | 506/18 |
| 5,858,653 A | 1/1999 | Duran et al. | |
| 6,083,726 A | 7/2000 | Mills, Jr. et al. | |
| 6,150,102 A | 11/2000 | Mills, Jr. et al. | |
| 6,214,187 B1 | 4/2001 | Hammond et al. | |
| 6,251,660 B1 | 6/2001 | Muir et al. | |
| 6,342,250 B1 | 1/2002 | Masters | |
| 6,368,356 B1 | 4/2002 | Zhong et al. | |
| 6,372,813 B1 | 4/2002 | Johnson et al. | |
| 6,391,937 B1 * | 5/2002 | Beuhler et al. | 522/152 |
| 6,410,044 B1 * | 6/2002 | Chudzik et al. | 424/423 |
| 6,537,747 B1 * | 3/2003 | Mills et al. | 506/43 |
| 6,696,285 B1 | 2/2004 | Mills, Jr. et al. | |
| 7,919,600 B2 * | 4/2011 | Mills et al. | 536/22.1 |
| 2003/0092838 A1 | 5/2003 | Fomperie et al. | |

FOREIGN PATENT DOCUMENTS

DE   19905793 A1 *   2/1999

OTHER PUBLICATIONS

"Biochemistry," Fourth Edition by Lubert Stryer, W.H. Freeman and Company, New York, 1995, pp. 75-90.*
"Chemistry," Six Edition by Brown, Lemay, and Burstein, Prentice Hall, Englewood Cliffs New Jersey, 1994, pp. 378.*
Lewin B. DNA is the genetic material. Genes IV, 4th edition, p. 57-74, 1990.*
Simmel, Fredrich C., et al.; "Using DNA to construct and power a nanoactuator"; Physical Review E, vol. 63, 2001 The American Physical Society; pp. 041913-1-041913-5.
Lewin, Benjamin, "DNA is the Genetic Material"; Genes IV, 4th edition, 1990; pp. 57-74.
Rehman, Farah N., et al.; "Immobilization of acrylamide-modified oligonucleotides by co-polymerization"; Nucleic Acids Research, 1999, vol. 27, No. 2, pp. 649-655.
Hammond, Phil et al.; "Acrydite Gel Technology: Accelerated hybridization using co-polymerized DNA probes"; Mosaic Technologies, Jan. 1998; pp. 1-14.
"Acrydite Modified Custom Oligonucleotides—An Overview of Acrylamide Attachment Chemistry"; Apogent Discoveries; 2001; pp. 1-4.
Bischoff, Farideh Z., et al.; "Cell-free fetal DNA in maternal blood: kinetics, source and structure"; Human Reproduction Update; European Society of Human Reproduction and Embryology 2004; pp. 1-9.
Muller, Jurgen R., et al.; "Stimulation of Murine B Lymphocytes induces a DNA Exonuclease Whose Activity on Switch-u DNA is Specifically Inhibited by Other Germ-Line Switch Region RNAs"; The American Association of Immunologists; The Journal of Immunology; 1998; pp. 3337-3341.
Rebowski, Grzegorz, et al.; "Antisense hairpin loop oligonucleotides as inhibitors of expression of multidrug resistance-associated protein 1: Their stability in fetal calf serum and human plasma"; Acta Biochimica Polonica—Reduction of MRP1 Expression; vol. 48 No. Apr. 2001; pp. 1061-1076.
Famulski, Konrad S., et al.; "Purification and characterization of a novel human acidic nuclease/intra-cyclobutyl-pyrimidine-dimer-DNA phosphodiesterase"; Biochem. J. (2000); pp. 583-593.
Kwon, Hyung-Joo, et al.; "Identification of an endonuclease secreted by human B lymphoblastic IM9 cells"; The International Journal of Biochemistry & Cell Biology 30 (1998); pp. 217-233.
Reynolds, Jason E., et al.; "Intracellular acidification is associated with, but not required for caspase activation, DNA fragmentation or apoptosis"; International Journal of Oncology 11 (1997); pp. 1241-1246.
Krieser, Ronald J., et al.; "Deoxyribonuclease II: structure and chromosomal localization of the murine gene, and comparison with the genomic structure of the human and three *C. elegans* homologs"; 2000 Elsevier Science, Gene 252 (2000); pp. 155-162.
Kirzon, SS, et al.; "Changes in the activity of endonucleosis of nuclear-dna in children with acute-leukemia" Gematologiya and Transfuziologiya, 40 (3): May-Jun. 8-10, 1995 (Abstract); 1 Page.

(Continued)

*Primary Examiner* — Prabha Chunduru
(74) *Attorney, Agent, or Firm* — Hitt Gaines, PC

(57) ABSTRACT

The present invention provides a composition for selectively delivering an active agent to a portion of an organism. The composition comprises first and second polymer portions, having first and second functional groups attached as a sidechain thereto, respectively. The first and second functional groups form cross-links between the first and second polymer portions. The cross-links are capable of being broken by a substance of the organism, thereby resulting in release of the active agent. The composition provides a novel means for controlling the selective release of the active agent in the organism.

13 Claims, 11 Drawing Sheets

OTHER PUBLICATIONS

Kim, Kwon HJ.; "Properties of the endonuclease secreted by human B lymphoblastic IM9 cells"; Journal of Biochemistry and Molecular Biology 31 (1): 106-110 Jan 31, 1998; 1 Page.

Uhlmann, Eugen, et al.; "Studies on the Mechanism of Stabilization of Partially Phosphorothioated Oligonucleotides Against Nucleolytic Degradation"; Antisense & Nucleic Acid Drug Development 7; 1997; pp. 345-350.

* cited by examiner

AGENT DELIVERY SYSTEM CAPABLE OF SELECTIVELY RELEASING AN AGENT

CROSS-REFERENCE TO RELATED APPLICATION

This application is a continuation-in-part of the disclosure of U.S. patent application Ser. No. 10/252,287, entitled, "COMPOSITIONS THAT REVERSIBLY GEL AND DE-GEL," to Allen P. Mills and Bernard Yurke ("Mills"), filed on Sep. 23, 2002, now U.S. Pat. No. 7,919,600 commonly assigned with the present invention, and incorporated by reference as if reproduced herein in its entirety.

TECHNICAL FIELD OF THE INVENTION

The present invention is directed, in general, to a composition for delivering a biologically active agent.

BACKGROUND OF THE INVENTION

Compositions are used extensively in a wide range of biomedical applications, for the delivery of diagnostic or therapeutic active agents. A longstanding problem in the manufacture of such compositions is the controlled delivery of the active agents to particular organisms or sites within organisms, such as a particular cell type. The timed release of active agents from such compositions, also remains problematic. These problems reside in part due to the manner in which such active agents are released from the composition.

Polymers may be cross-linked to form compositions that serve as a matrix or reservoir for delivery of a drug over a sustained period. For example, cross-linked hydrogels of polyacrylamide, are capable of absorbing a substantial amount of water to form elastic or inelastic compositions. The compositions may absorb water and swell to thereby release the drug incorporated therein. Unfortunately, the hydrogels may have a number of undesirable characteristics.

For example, some such compositions are not biodegradable. Therefore, the removal of the compositions from an organism requires excretion of the composition. Other compositions require the use of undesirable solvents or monomers during manufacture. For instance, a conventional manufacture of polyacrylamide uses the monomer acrylamide and cross-linker N, N' methylbisacryamide. Residual amounts of the unreacted monomer and cross-linker typically remain in the final composition and can cause damage in surrounding tissues or inactivation of the active agent incorporated into the composition.

Moreover, the preparation of such compositions may preclude inclusion of the active agent during formation of the matrix. For example, the conventional preparation of a polyacrylamide gel involves formation of a free radical on the growing polymer chain and cross-linking chains. Such a process could chemically alter and inactivate an active agent present during the gel's formation. Therefore, additional processing steps are typically taken to first prepare a capsule and then add the active agent to the capsule, usually along with waxes, fats or other fillers, to help the capsule maintain its shape. Furthermore, because the release of the active agent from certain gels is governed by diffusion, release is not targeted to a particular area of the body of an organism.

Accordingly, one objective of the invention is a process for making a composition capable of forming a gel in the presence of an active agent without deleteriously effecting the active agent. Another objective of the invention is a composition that enables a targeted release of an active agent included therein.

SUMMARY OF THE INVENTION

To address the above-discussed deficiencies, one embodiment of the present invention provides a composition comprising a first polymer portion having first functional groups attached as side-chains thereto and a second polymer portion having second functional groups attached as side-chains thereto. The first and said second functional groups are capable of forming cross-links between the first and second polymer portions. An active agent is disposed between the first and second polymer portions. The active agent is capable of being released by an interaction of a substance with the first or second polymer portions.

In another embodiment, the invention further provides a method for delivering an active agent to an organism. The method includes introducing a composition into an organism. The composition comprises a first and second polymer portion and an active agent as described above. The organism includes a substance capable of releasing the active agent from said composition by breaking the cross-links between first and second polymer portions.

BRIEF DESCRIPTION OF THE DRAWINGS

The invention is best understood from the following detailed description, when read with the accompanying FIGURES. Various features may not be drawn to scale and may be arbitrarily increased or reduced for clarity of discussion. Reference is now made to the following descriptions taken in conjunction with the accompanying drawings, in which:

FIG. 1' schematically illustrates the cross-linking of two nucleic acid sequence-modified polymers comprising a composition formed by complementary base pairing of the sequences together according to the present invention.

FIG. 2' schematically illustrates the cross-linking of two nucleic acid sequence-modified polymers comprising a composition formed by complementary base pairing of the sequences to a third nucleic acid sequence according to the present invention;

DETAILED DESCRIPTION

The present invention recognizes the advantageous use of an active agent delivery system that includes a composition of the present invention. The composition has functional groups, attached as side-chains to a polymer portions, so as to dispose or contain an active agent in the composition. Such compositions may be reversibly changed from a fluid to a solid gel state by cross-linking the polymers, as facilitated by interactions between the functional groups. The solid gel state is achieved without changes in temperature, the generation of undesirable free radicals or other intermediary chemicals. Thus, such compositions may be advantageously used as materials for the delivery of active agents to organisms.

The present invention further recognizes that the release of an active agent may be controlled by a substance that breaks the cross-links of the gel, for example, by cleaving one or more of the functional groups. When the substance is an enzyme, in addition to facilitating the release of the active agent, the enzymatic cleavage of the crosslinking functional groups facilitates the removal of the delivery system from the organism. Moreover, the delivery system may be used to advantageously target the release of the active agent, to a particular location in the organism, thereby reducing potential systemic side-effects associated with a non-targeted release of the active agent.

Preferably, the cross-link is formed by a plurality of reversible cross-links, such as hydrogen bonds, between the first and second functional groups. By forming the cross-link, the active agent is contained within the composition. Containment may be achieved by physically restricting the active agent within the internal structure of the composition, by chemical interactions between the active agent and the composition or a combination of both. Alternatively, as further illustrated below, the active agent may comprise a portion of the functional groups attached as side-chains to the first or second polymer.

Figure 1:
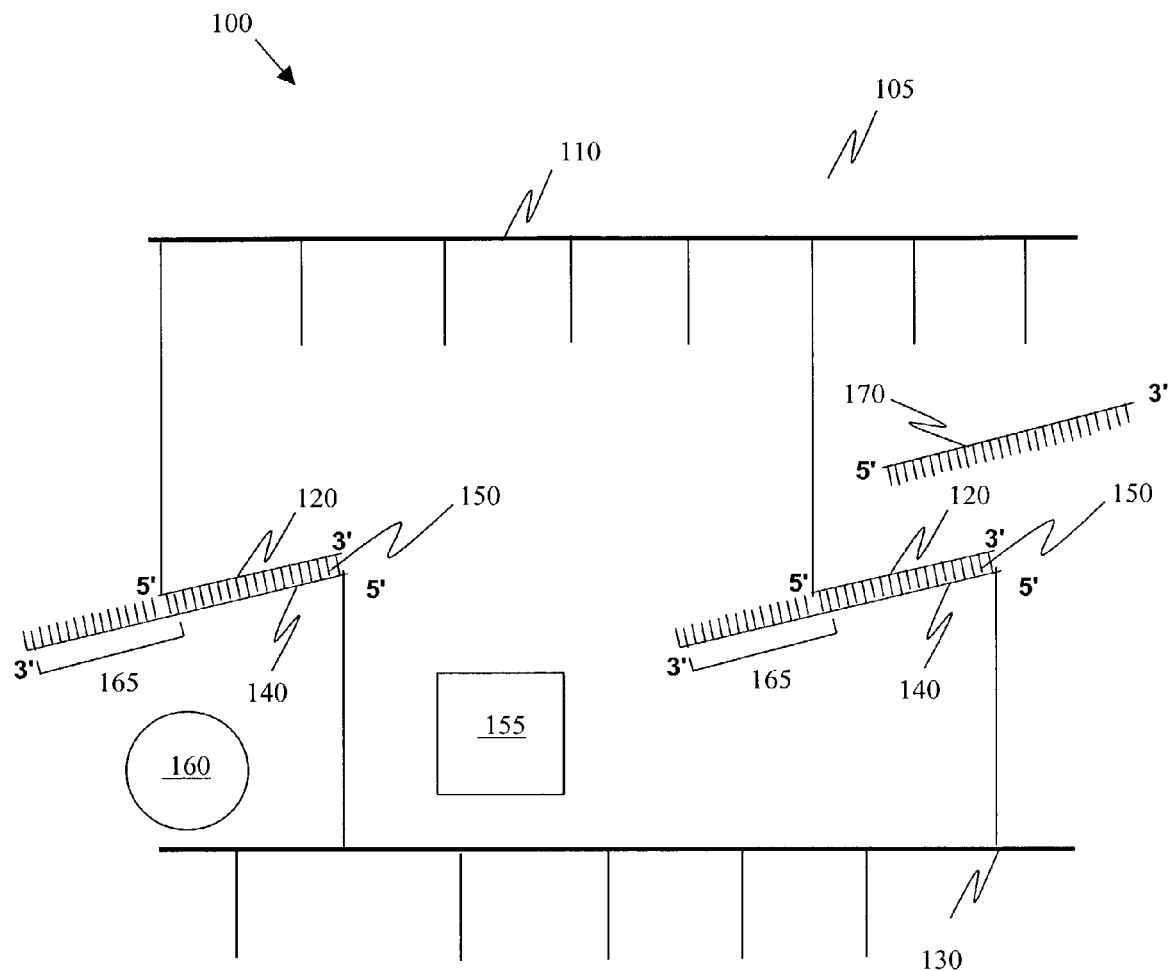
FIG. 1 schematically illustrates a detail view of a portion of a composition of the present invention.
Figure 1:
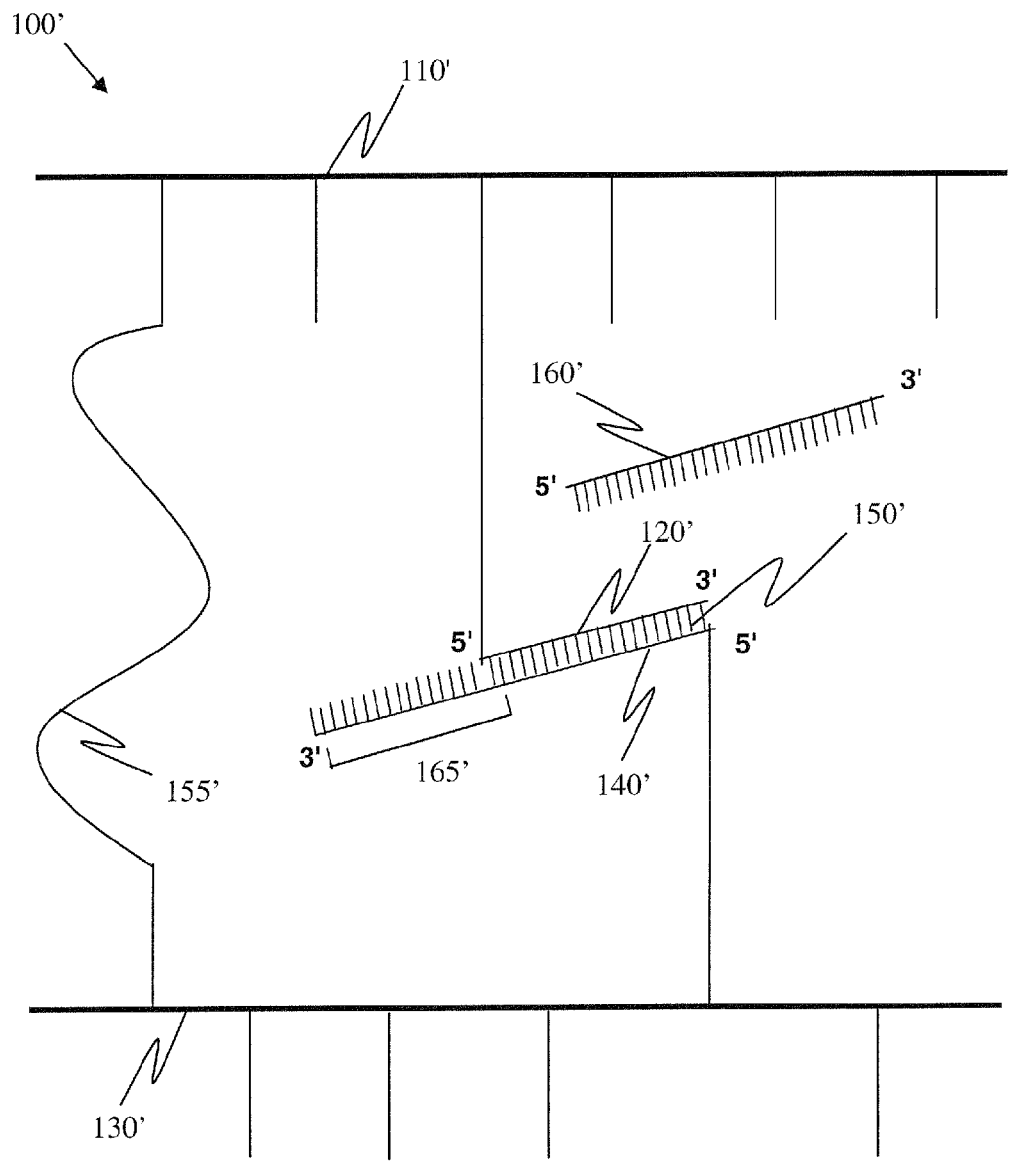

Certain preferred embodiments of the present invention recognize the advantageous use of functional groups comprising nucleic acid sequences, attached as side-chains to polymers, to produce compositions. FIG. 1 illustrates a schematic representation of a portion of one such active agent delivery system 100. The composition 105 comprises a first polymer portion 110 having a first functional group comprising a nucleic acid sequence 120 attached as a side-chain thereto. The composition 105 further comprises a second polymer portion 130 having a second functional group comprising a nucleic acid sequence 140 attached as a side-chain thereto. The first and said second nucleic acid sequences 120, 140 are capable of forming a cross-link 150 between the first and second polymer portions 110, 130. The first and second polymer portions 110, 130 may comprise any polymer to which the nucleic acid sequences 120, 140 can be attached as side-chains thereto. The first and second polymer portions 110 may comprise a single polymer or comprise two or more separate polymers. Additionally, the first and second nucleic acid sequences 120, 140 may be distributed on the entire length of such polymer or polymers, or only on the first and second portions 110, 130.

An active agent 155 contained by the composition 105, is released by an interaction between an external substance 160 and the composition 105. The substance 160 may be a wide range of organic or inorganic compounds that are capable of breaking the cross-link 150. In a more specific embodiment, the substance 160 is capable of breaking hydrogen bonds between the first and second functional groups 120,140. Other examples of the substance 160 are also discussed below.

In certain preferred embodiments, the substance 160 is an enzyme capable of breaking the cross-link 150 by a cleavage of the first or said second functional groups 120, 140. The term enzyme as used herein, refers to any protein or ribozyme (i.e., molecular weight greater than about 1000 g/mole) capable of catalyzing the cleavage of the functional groups that crosslink the first and second polymer 110, 130. The enzyme may be naturally occurring or synthetically produced. In certain preferred embodiments, the enzyme is present in or released by an organism that is a target of the active agent. The organism may be an individual cell, such as a bacterium, a virus, or a collection of cells found in particular organs of higher animals, including man or domestic animals, or plants. The enzyme may be released from a cell selected from the group consisting of a cell in a digestive tract, for example the digestive tract of ruminants, or of a cell undergoing apoptosis, for example a cell following ischemia. Alternatively, the enzyme may be presented to the organism by artificial means, for example, via an injection of the enzyme itself, a precursor of the enzyme, or a second organism or other delivery system that releases the enzyme.

In certain embodiments, the enzyme may be a nuclease or a ribozyme. The term nuclease as used herein refers to any protein capable of promoting the cleavage of linkages in a nucleic acid sequence. The manner in which such cleavage occurs is well-know to those of ordinary skill in the art. Nucleases, for example, may cleave the phosphodiester bonds between nucleotide subunits of nucleic acids. Any of several classes of nucleases, such as endonucleases and exonucleases, may hydrolyze nucleic acids. In certain embodiments, for example, the nuclease may be selected from EC 3.1.11 to EC 3.1.31, using the nomenclature defined by the International Union of Biochemistry and Molecular Biology and published in Enzyme Nomenclature (1992) including Supplement 1 (1993), Supplement 2 (1994), Supplement 3 (1995), Supplement 4 (1997) and Supplement 5 (in Eur. J. Biochem. 1994, 223, 1-5; Eur. J. Biochem. 1995, 232, 1-6; Eur. J. Biochem. 1996, 237, 1-5; Eur. J. Biochem. 1997, 250; 1-6, and Eur. J. Biochem. 1999, 264, 610-650; respectively), all of which are incorporated herein by reference.

The term ribozyme as used herein refers to any nucleic acid sequence capable of promoting the cleavage of linkages in a nucleic acid sequence. Numerous classes of such nucleic acid sequences, such as ribonucleic acid (RNA), are well known to those of ordinary skill in the art. Non-limiting examples include Group I and II Introns, RNAase P, Hammerhead ribozymes, Hairpin ribozymes, Hepatitis Delta Virus produced ribozymes, or Neurospora-derived ribozymes.

In certain preferred embodiments, for example, when the first and second functional groups 120, 140 comprise single stranded nucleic acid sequences, the enzyme is capable of selectively cleaving a specific nucleic acid sequence in the first or second nucleic acid sequence 120, 140. For example, certain nucleases termed restriction endonuclease, commonly found in certain bacteria, recognize specific, short nucleotide sequences and cleave DNA at discreet locations in the sequence. In other preferred embodiments, the enzyme may comprise a first enzyme capable of selectively cleaving the first nucleic acid sequence 120 and a second enzyme capable of selectively cleaving the second nucleic acid sequence 140.

The release of the active agent 155 can be controlled by controlling the catalytic activity of the enzyme for the cleavage of the functional groups. For example, if the active agent 155 is to be released at a particular cell that produces a certain nuclease, then the particular order of base pairs in one or both of the first or second nucleic acid sequences 120, 140 can be selected such that the activity of the nuclease for the nucleic acid sequences is increased or decreased. Accordingly, the release of the active agent 155 from the composition 105 can be increased or decreased upon interaction of the nuclease with the composition 105.

Any of the embodiments of the composition 105 described in Mills may be used in the delivery system of the present invention to control the release of the active agent 155. In certain preferred embodiments, for example, the substance 160 is a third nucleic acid sequence 170, serving as a removal strand. In such embodiments, at least one of the first or second nucleic acid sequence 120, 140 further comprises a toe-hold nucleic acid sequence 165. The third nucleic acid sequence 170 is complementary to the toe-hold sequence 165 and the remainder of the first or second nucleic acid sequence 120, 140 comprising the toe hold sequence 165, so the third nucleic acid sequence 170 can bind at the toe-hold sequence 165 and thereby dissociate the cross-link 150. In certain preferred embodiments, the third nuclei acid sequence 170 is messenger RNA (mRNA). Thus, for example, the expression of a particular gene by a cell or organism embodied in mRNA production could cause the disassembly of the composition 105.

The active agent 155 may comprise any compound or group of compounds with structures that are contained by the composition 105. Preferably, the active agent 155 is a chemically active compound selected from the group consisting of: biochemical or chemical compounds, preferably with diagnostic or therapeutic properties, preferably suitable for identifying or therapeutically treating pathogens and toxins from biological fluid. Examples of suitable active agents include drugs, antibiotics or genes.

In certain embodiments, the active agent 155 may comprise a nucleic acid sequence released from the first or the second nucleic acid sequence 120, 140 by the interaction between a substance 160 comprising an enzyme and the composition 105.

Figure 2:
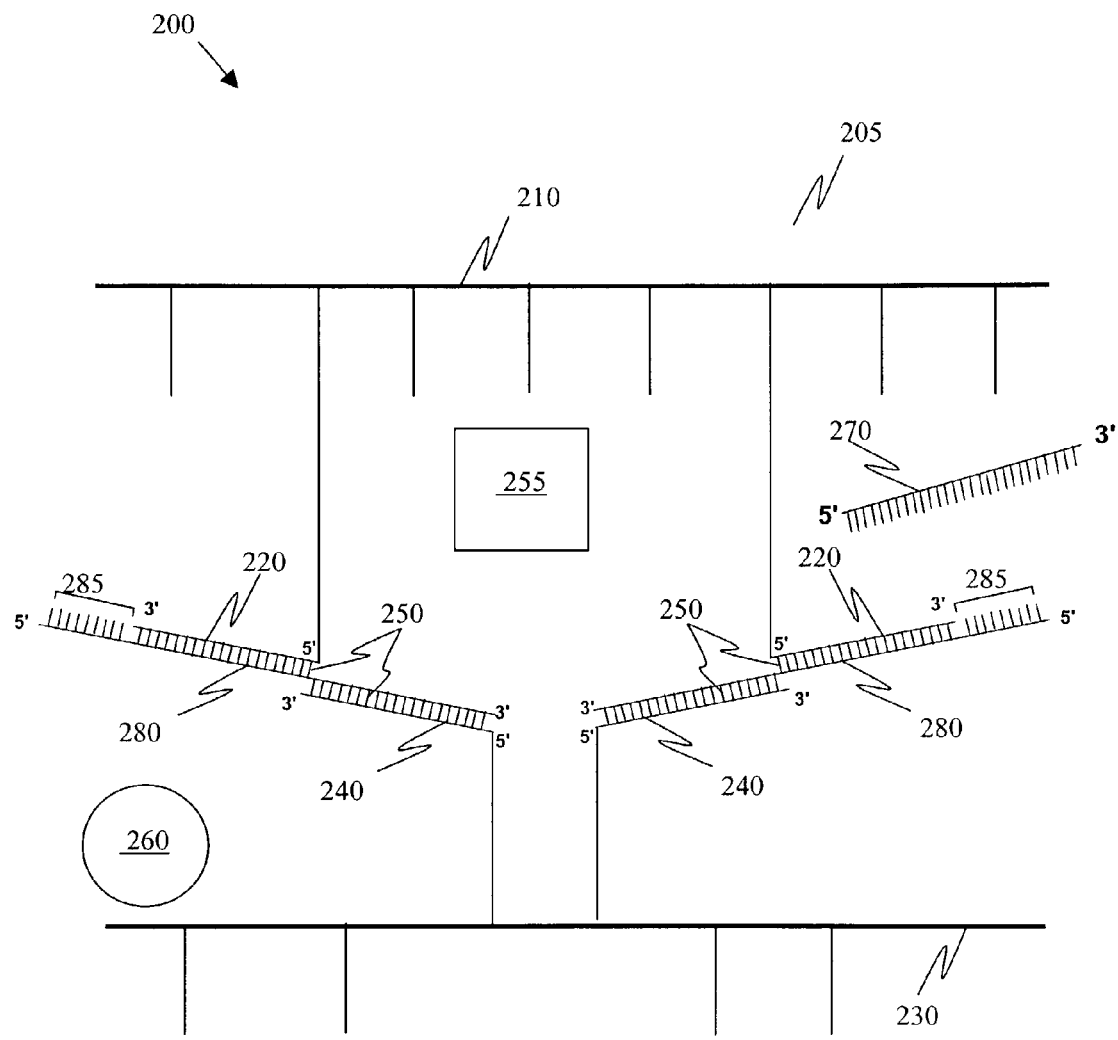
FIG. 2 schematically illustrates a detail view of a portion of an alternative composition of the present invention.
Figure 2:
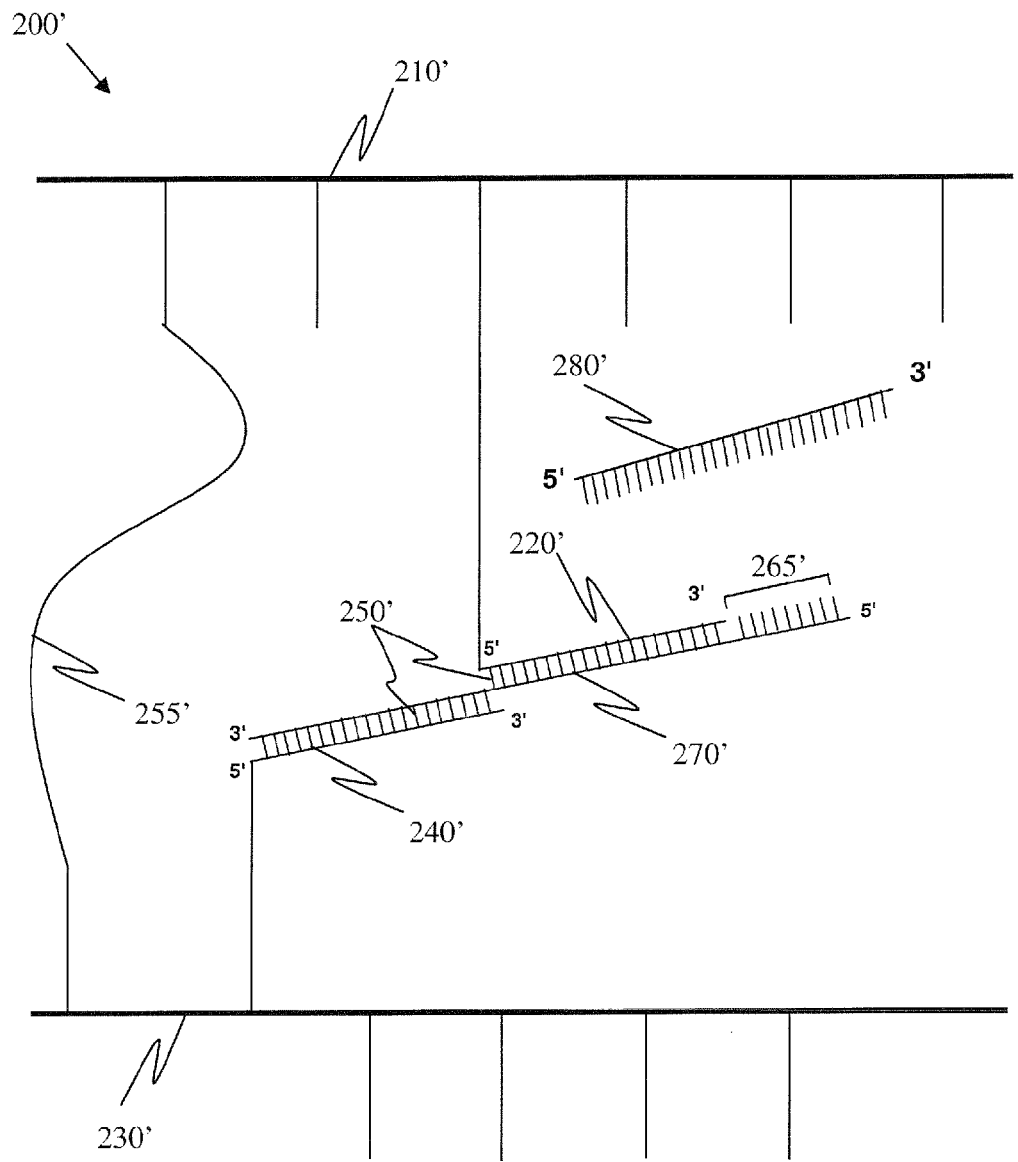

In alternative preferred embodiments of the delivery system 200, as illustrated in FIG. 2, where like reference numbers refer to like elements shown in FIG. 1, the composition 205 may further include a third nucleic acid sequence 280, serving as a linking strand. The third sequence attaches to the first and to the second nucleic acid sequences 220, 240 to facilitate formation of the cross-link 250. In turn, the cross-link 250 is capable of being broken by a cleavage of the third nucleic acid sequence 280 by a substance 260 comprising an enzyme. Alternatively the substance 260 may comprise a fourth nucleic acid sequence 270.

Analogous to that described above for the system 100 presented in FIG. 1, the fourth nucleic acid sequence 270 is complementary to a toe-hold 285 nucleic acid sequence and the remainder of the third nucleic acid sequence 280. Thus, binding of the fourth nucleic acid sequence 280 causes dissociation of the cross-link 250. Thus, the fourth sequence 280 serves as a removal strand.

Another embodiment of the present invention is a method for delivering an active agent to an organism. The method includes introducing a composition into an organism. The composition comprises a first polymer portion having first functional groups attached as a side-chain thereto and a second polymer portion having second functional groups attached as a side-chain thereto. An active agent is disposed between the polymer portions, the first and the second functional groups forming a cross-link between the first and the second polymer portions. The organism includes a substance capable of releasing the active agent from the composition by breaking the cross-links.

In certain preferred embodiments, the method for the delivering an active agent to an organism can be targeted to particular cells in the organism, for example, because the substance is an enzyme that is produced in or released by cells in the organism that are a target for presentation of the active agent thereto. For instance, the enzyme may be released from a cell selected from a cell in a digestive tract or a cell undergoing apoptosis.

In certain preferred embodiments, the release of the active agent is a function of a catalytic activity of the enzyme for the cleavage of the first and second functional groups. In turn, the catalytic activity of the enzyme for cleavage of the nucleic acid sequences can be controlled by selecting particular nucleic acid sequences used for cross-linking. Knowledge of the specificity of the enzyme produced in or released by the target cells, for example, would allow the selection of a nucleic acid sequence that is more or less readily cleaved by the enzyme. Thus, in certain embodiments, the enzyme is capable of selectively cleaving a specific nucleic acid sequence in the first nucleic acid sequence or the second nucleic acid sequence. Alternatively, there may be a first enzyme that selectively cleaves the first nucleic acid sequence and a second enzyme that selectively cleaves the second nucleic acid sequence.

Releasing the active agent may be achieved by interacting the composition with a substance comprising a third polymer having a third functional group, such as a nucleic acid sequence, attached as a side-chain thereto. In such embodiments, one of the first or second nucleic acid sequences has a toe-hold sequence sufficiently complementary to the third sequence that the latter facilitates dissociation of the cross-link.

Alternatively, as noted in Mills and elsewhere herein, the third polymer has third functional groups attached as chains thereto. For example, a third nucleic acid sequence serves as a linking strand by attaching to the first and the second nucleic acid sequences to form the cross-link. In such embodiments, cross-link may be broken by a cleavage of said third nucleic acid sequence by a substance that is one of the target organism's enzymes. Alternatively, the release of the active agent in such embodiments can be achieved by a substance that acts as a removal strand. For the substance may be a fourth nucleic acid sequence such as discussed above. In such embodiments, the third nucleic acid sequence includes a toe-hold sequence complementary to a portion of the removal strand.

One embodiment of the present invention is directed to a composition comprising a first and second polymer having first and second functional groups attached as side-chains thereto, respectively. The first and second functional groups are capable of reversibly forming a cross-link between the first and second polymers. The composition can change thereby from a viscous fluid state to a solid gel state as interactions between the functional groups cause more cross-linking between the polymers. The gel state may be achieved without changes in temperature (e.g., no cooling of the gel is required) and without the generation of undesirable free radicals or other intermediary chemicals. Moreover, the gel may be transformed back to the liquid state without heating the gel. Such gel compositions may be advantageously used as biomaterials for the delivery of agents to organisms or as a prosthetic device, and in electronic or optoelectronic devices.

Preferably, the cross-link is formed by a plurality of hydrogen bonds between the first and second functional groups. In certain embodiments, the addition of a substance causes the first and second functional groups to reversibly bind. Certain preferred embodiments of the present invention recognize the advantageous use of functional groups comprising nucleic acid sequences, attached as side-chains to polymers, to produce compositions.

FIGURE 1' illustrates a schematic representation of a portion of one such composition 100'. The gel composition 100' comprises a first polymer 110' having a first functional group comprising a nucleic acid sequence 120' attached as a side-chain thereto. The composition 100' further comprises a second polymer 130' having a second functional group comprising a nucleic acid sequence 140' attached as a side-chain thereto. The first and said second nucleic acid sequences 120', 140' are capable of reversibly forming a cross-link 150' between the first and second polymers 110', 130'. The first and second polymers 110', 130' may comprise any polymer to which the nucleic acid sequences 120', 140' can be attached as side-chains thereto. In some preferred embodiments, for example, the first and second polymers 110', 130' may comprise a polymethylmethacrylate. In other preferred embodiments the first and second polymers 110', 130' comprises a polyacrylamide. In still other preferred embodiments, the first and second polymers 110', 130' comprised a polyvinyl alcohol. Other combinations are possible, where the first and second polymers 110', 130' are different polymers, for example, where the first polymer 110' is polyacrylamide while the second polymer 130' is polymethylmethacrylate.

In preferred embodiments such as that illustrated in FIG. 1', the first and said second nucleic acid sequences 120', 140' are capable of hybridizing to form reversible cross-links 150' comprising hydrogen bonds between complementary base portions of the first and the second nucleic acid sequences 120', 140'. The term hybridization as used herein refers to the annealing of single-stranded nucleic acid fragments to form a double-stranded structure. The formation of such hydrogen bonds to form nucleic acid duplex structures is well known to those of ordinary skill in the art, and therefore need not be further explained herein. Depending on the length and identity of the nucleic acid sequence and environmental conditions under which the, hybridization is performed (such as pH, ionic strength and temperature), the amount of base mismatch may range from 0% ("high complementarity") to up to 99% ("low complementarity"), and more preferably less than about 50% mismatch.

The first and said second nucleic acid sequences 120', 140' may separately comprise any naturally occurring nucleotide oligomers, or synthetically modified analogs of the oligomers. In certain preferred embodiments, for example, the nucleic acid sequences 120', 140' are separately selected from the group consisting of deoxyribonucleic acid (DNA); ribonucleic acid (RNA); peptide nucleic acids (PNA) and phosphorothioate analogs of DNA. The bases associated with the nucleotides comprising the nucleic acid sequences 120', 140' may comprise any naturally occurring nitrogen containing bases, such as purines or pyrimidines, or synthetically modified analog of the bases. In certain preferred embodiments, for example, where the one or both of the nucleic acid sequences 120', 140' comprise deoxyribonucleic acid, the bases may comprise adenine (A), guanine (G), cytosine (C), and thymine (T). In other preferred embodiments, for example, where one or both the nucleic acid sequences 120', 140' comprises ribonucleic acid, the thymine (T) base may be replaced by uracil (U).

The cross-links 150' have an association rate and a dissociation rate that are functions of a length of the first nucleic acid sequence 120' and a length of the second nucleic acid sequence 140'. The term length as used herein refers to the number of bases present in the nucleic sequence of interest. In general, the longer the sequence, the slower the association and dissociation rate. Those of ordinary skill in the art understand that the rate of association and disassociation of nucleic acid sequences depends on the length of the DNA strands, the base sequence, and the degree of complementarily.

In addition, the cross-links 150' have an association rate and a dissociation rate that are functions of a percentage of complementarily between the first nucleic acid sequence 120' and the second nucleic acid sequence 140'. Preferably, a sequence of at least ten bases in the first nucleic acid sequence is complementary to at least a portion of bases in the second nucleic acid sequence. More preferably, the percentage of complementarily between the first nucleic acid sequence 120' and the portion of bases in the second nucleic acid sequence 140' is at least about 50% and even more preferably at least about 99% complementary.

Moreover, the first nucleic acid sequence 120' and said second nucleic acid sequences 140' preferably has a minimal percentage of internal complementarily. Minimizing internal complementarily helps to prevent the formation of hairpin structures within either sequence. Preferably, the internal complementarily is less than 30% and even more preferably less than about 10%.

To promote the formation of the cross-link 150' between the first polymer 110' and the second polymer 130', in certain embodiments, the first nucleic acid sequence 120' and the second nucleic acid sequence 140' each comprise between about 5 and about 100 nucleotide bases. More preferably, they comprise between about 20 and about 30 nucleotide bases in length.

More than one pair of complementary nucleic acid sequences 120', 140' may be attached as side-chains to the first and second polymer 110', 130' to facilitate crosslinking. For example the side-chains of the first polymer 110' may comprise at least two first nucleic acid sequences 120' having at least one difference in a base sequence between he two first nucleic acid sequences 120'. Similarly, the side-chains of the second polymer 130' may comprise at least two second nucleic acid sequences 140' having at least one difference between the two second nucleic acid sequences 140'. Furthermore, crosslinking may further include a combination of cross-links 150' between nucleic acid sequences 120', 140', as discussed above, and conventionally formed cross-links 155' achieved, for example, through the addition of N, N' methylene bis acrylamide during polymerization of the first and second polymers 110', 130'. Such embodiments advantageously allow for further adjustment of the transition of the composition from liquid to solid, as well to adjust the chemical and mechanical properties of the composition.

The dissociation of the cross-links 150' between the first and second polymer 110', 130' may be facilitated with the addition of a third nucleic acid sequence 160'. Alternatively, the third nucleic acid sequence 160' may deter or prevent the formation of the cross-link 150'. In certain embodiments, the third nucleic acid sequence 160' has between about 2 and about 20 nucleotide bases. Preferably, the third nucleic acid sequence is within 6 base pairs in length, and more preferably the same length as at least one of the first or second nucleic acid sequence 120', 140'.

At least one of the first nucleic acid sequence 120' or the second nucleic acid sequence 140' further comprise a toe-hold nucleic acid sequence 165'. The toe-hold nucleic acid sequence 165' is sufficiently complementary to the third nucleic acid sequence 160' that the third nucleic acid sequence 160' facilitates a dissociation of the cross-link 150'. The extent of complementarily between the third nucleic acid sequence 160' and toe-hold nucleic acid sequence 165' is at least about 50% and more preferably at least about 90%, and may be adjusted to control the rate or the effectiveness of the breaking of the crosslink.

The toe-hold nucleic acid sequence 165' provides a region to which third nucleic acid sequence 160' can initially bind. Once the third nucleic acid sequence 160' has hybridized with the toe-hold nucleic acid sequence 165', the third nucleic acid sequence 160' competitively binds to remaining portions of one or both of the first and second nucleic acid sequences 120', 140'. This competition causes unbinding of the first and second nucleic acid sequences 120', 140' and dissociation of the cross-link 150'. The toe hold sequence is preferably shorter than the third nucleic acid sequence 160'.

An alternative preferred embodiment of the gel composition 200', is illustrated in FIG. 2', wherein the reference numbers refer to like elements of the embodiment depicted in FIG. 1'. Here, the gel composition 200' further includes a third nucleic acid sequence 270' that, when attached to the first and the second nucleic acid sequences 220', 240', facilitates formation of the cross-link 250'. In this embodiment, therefore, the cross-link 250' includes the nucleotide backbone of the third nucleic acid sequence 270' and a plurality of hydrogen bonds between the third nucleic acid sequence 270' and the first and second nucleic acid sequence 220', 240'. The third nucleic acid sequence 270' may be of any length sufficient to facilitate formation of the cross-link 250'. In certain preferred embodiments, for example, the length of the third nucleic acid sequence 270' is at least as long as the combined length of the first and second nucleic acid sequences 220', 240'.

Such alternative gel compositions 200' may further include a fourth nucleic acid sequence 280' that facilitates dissociation of the cross-links 250' between the first and second polymer 210', 230'. Analogous to that discussed for the embodiment shown in FIG. 1', the third nucleic acid sequence 270' may further comprise a toe-hold nucleic acid sequence 265' that is sufficiently complementary to the fourth nucleic acid sequence 280' that the fourth nucleic acid sequence 280' facilitates a dissociation of the cross-link 250'.

Certain preferred embodiments use the gel composition in a prosthetic device and electronic or optoelectronic devices. As further explained below, the prosthetic device may be capable of changing shape as a function of the extent of the cross-links 150' formed between first and the second polymers, 110', 130', via interactions between the first, second and third nucleic acid sequences 120', 140', 160' (FIG. 1'), or via analogous interactions for the embodiment shown in FIG. 2'. In certain embodiments, the prosthetic device may be capable of changing elastic modulus as a function of the extent of the above-mentioned cross-links. Non-limiting examples of the prosthetic device include: artificial spinal disk fluid; artificial ligaments; artificial bone; artificial valves; artificial skin; and dental prostheses.

Figure 3:
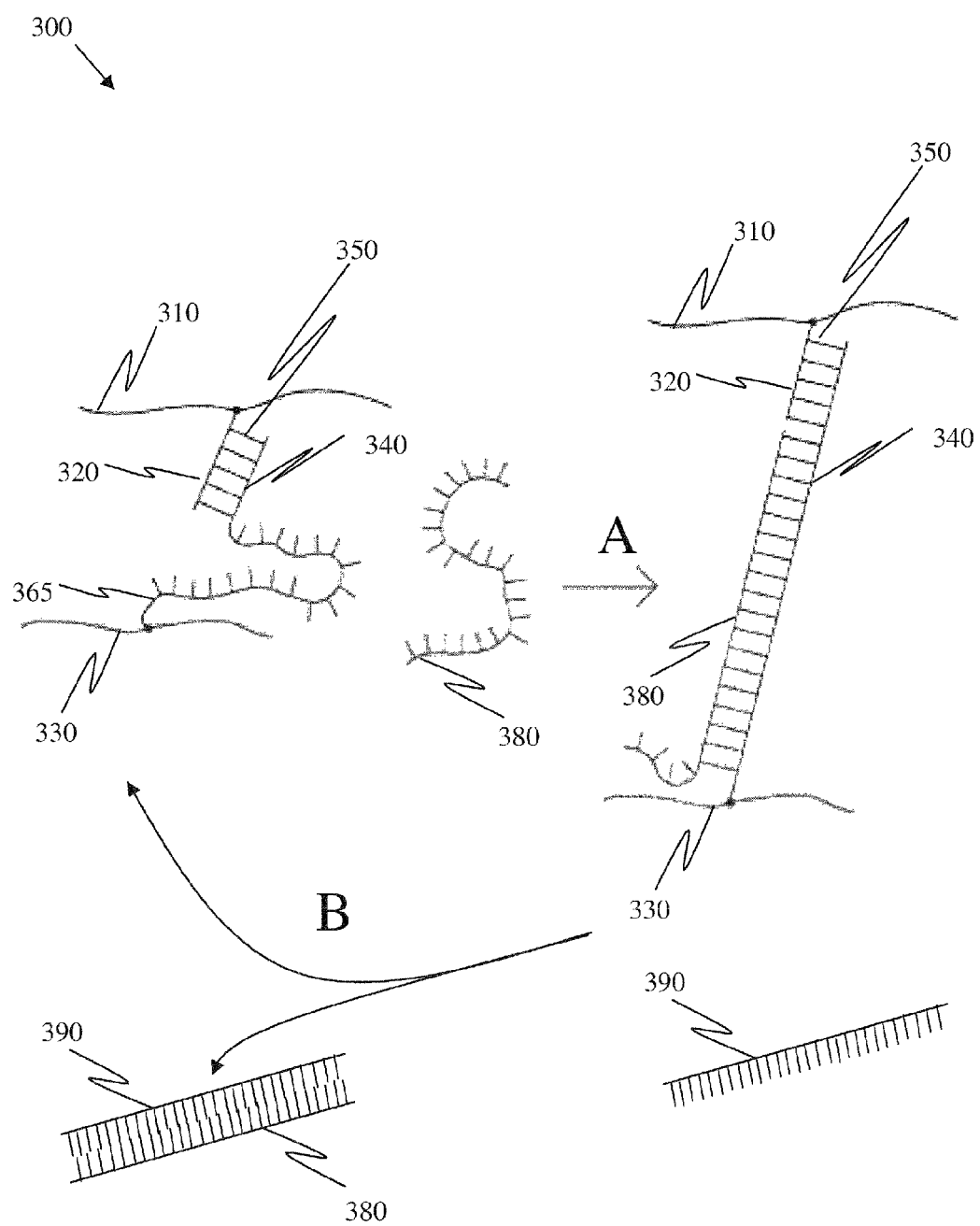
FIG. 3 schematically illustrates the swelling and shrinkage of a gel composition according to the present invention.

FIG. 3 illustrates one embodiment of how hybridization can cause the gel 300 to expand. The gel 300 has analogous structures and numbering scheme as discussed for FIG. 1'. Such embodiments may further include a fourth nucleic acid sequence 380, preferably having about the same length and being complementary to the toe-hold nucleic acid sequence 365. The fourth nucleic acid sequence 380, rather than serving as a strand to break the crosslink, serve to straighten the toehold 365, so that the first polymer 310 and the second polymer 330, are pushed apart, thereby causing swelling of the composition 300 (arrow A).

Moreover, in such embodiments, the addition of a fifth nucleic acid sequence 390 that is complementary to the fourth nucleic acid sequence 380, could cause shrinkage of the composition 350 (arrow B). When the third and fourth nuclei acid sequences 390, 380 hybrid with each other, the first and second polymer 310, 330 would come closer together because of the conversion from a stiff double stranded section of the first or second nuclei acid sequence 320, 340, back to a more flexible single stranded section, thereby causing the composition 300 to shrink (arrow B).

Figure 4:
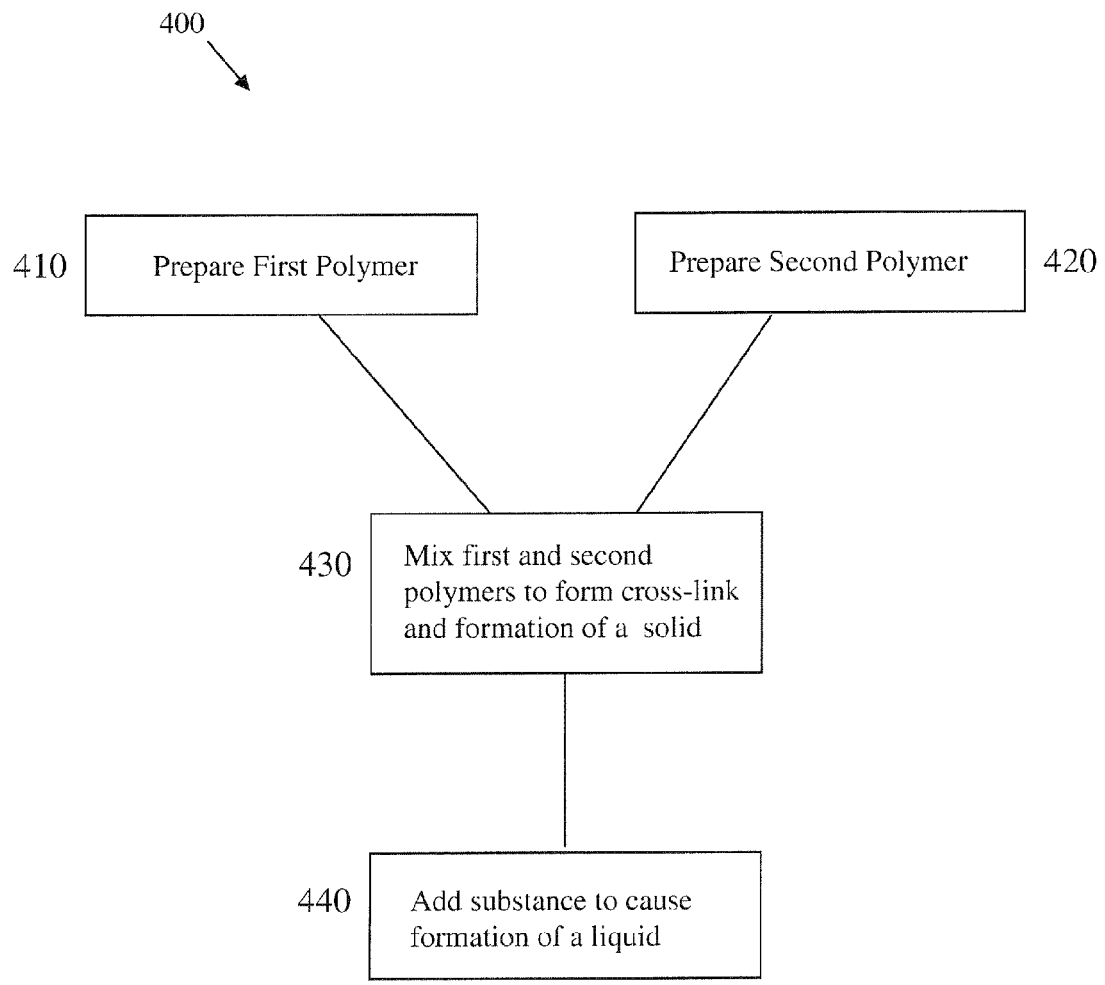
FIG. 4 illustrates, by flow diagram, a method for making a composition of the present invention.

Turning now to FIG. 4, illustrated is another embodiment of the present invention, a method 400 for making a composition. The method 400 comprises a step 410 of preparing a first polymer having first functional groups attached as side-chains thereto. In step 420, a second polymer having second functional groups attached as side-chains thereto is prepared. In step 430, the first and second polymers are mixed under conditions that cause the first functional groups to reversibly crosslink to the second functional groups. Preferably, the mixing causes the composition to change from a liquid to a solid.

Numerous methods, well known to those of ordinary skill in the art, may be used to prepare the first polymer and the second polymer in steps 410 and 420. Steps 410 and 420 may include modifying nucleic acid sequences with functional groups and attaching the functionalized nucleic acid sequences as side-chains to the first and second polymer or to monomeric units of the first and second polymer. In the latter such embodiments, preparation steps 410 and 420 then include separately mixing monomers of the first and second polymers with the functionalized first and the second nucleic acid sequences, respectively. The preparation steps 410, 420 may include adding a polymerization initiator and catalyst. The functional groups facilitate attachment of the modified first and second nucleic acid sequences as side-chains to the growing first and second polymers.

Exemplary functionalizations include: biotin-modified nucleic acid sequences non-covalently complexed with polymer comprising a protein, such as Streptavidin; thiol-modified nucleic acid sequences covalently linked via a disulfide bond to a polymer containing thiol groups; amine-modified nucleic acid sequences covalently linked to an activated carboxylate or an aldehyde group attached to a polymer; or the covalent attachment of nucleic acid sequences to polymers via acrylic linkages.

In certain preferred embodiments, the nucleic acid sequences are modified with a phosphoramidite having a general formula $CH_3-C(=CH_2)-CO-NH-(CH_2)_n-PO_4$, wherein n ranges from 1 to 18. One preferred phosphoramidite is $(CH_3-C(=CH_2)CO-NH-(CH_2)_6-PO_4$. The phosphoramidite may be copolymerized with a monomer comprising acrylamide to form a polyacrylamide polymer having first and second nucleic acid sequences attached as side-chains thereto. When the monomer is acrylamide, the initiator preferably comprises ammonium persulfate and the catalyst preferably comprises tetra ethylenediamine. Alternatively, the phosphoramidite-modified nucleic acid sequences can be reacted with a thiol to produce a thioether adduct that can then be bonded to monomers for subsequent use in polymerization.

The concentration of nucleic acids incorporated as side-chains into the polymer is determined by the ratio of moles of phosphoramidite modified nucleic acid sequences to moles of monomer. For example, the ratio of moles of the first and second nucleic acid sequence to moles of the acrylamide monomer, preferably ranges from about 1:1 to about 1:100.

As illustrated in FIG. 4, the method 400 may further include a step 440 of adding a substance that causes the first and second functional groups to unbind. Preferably the addition of the substance cause the solid gel to be converted to a liquid. In certain preferred embodiments, the substance is a third nucleic acid sequence, such as the third nucleic acid sequence 160 depicted in FIG. 1'. In such embodiments, as noted elsewhere herein, preferably one or both of the first or second nucleic acid sequences further comprise a toe-hold nucleic sequence.

Figure 5:
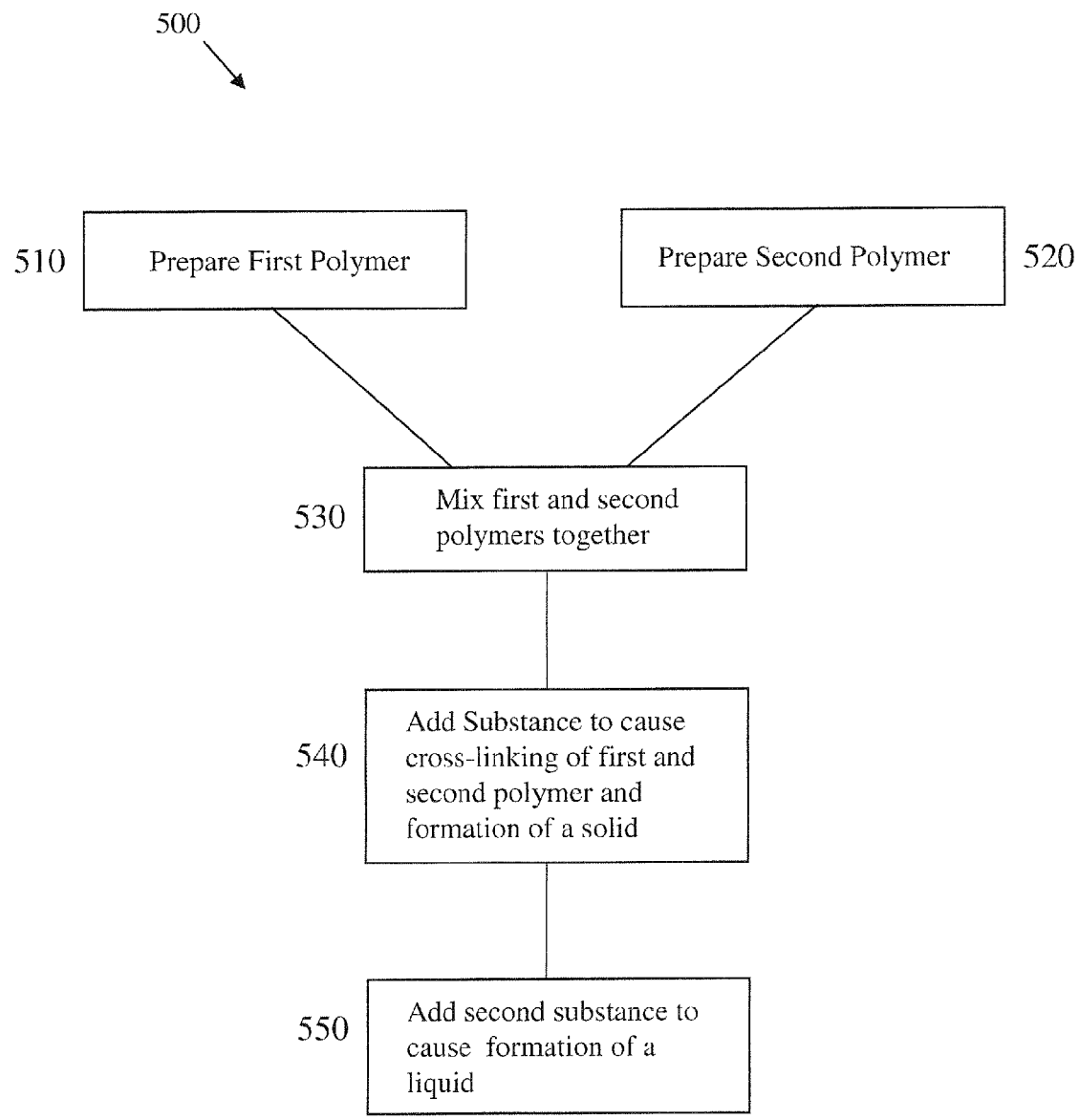
FIG. 5 illustrates, by flow diagram, a second method for making a composition of the present invention.

Another method 500 for making a composition according to the present invention is illustrated in FIG. 5. In step 510, a first polymer having first functional groups attached as side-chains thereto is prepared. In step 520, a second polymer having second functional groups attached as side-chains thereto is prepared. In step 530, the first and second polymers are mixed together. In step 540, a substance is added under conditions that cause the first and second functional groups to reversibly cross-link to the substance.

In one preferred embodiment of the method 500, the first and second functional groups are first and second single stranded nucleic acid sequences and the substrate is a third nucleic acid sequence, such as the third nucleic acid sequence 270' depicted in FIG. 2'. The third nucleic acid sequence is capable of attaching to the first and second nucleic acid sequences to facilitate formation of the cross-link. Certain embodiments may further include a step 550, of adding a second substance, for example, a fourth nucleic acid sequence, that facilitates a dissociation of the cross-link. Analogous to previously discussed embodiments, the third nucleic acid sequence further comprises a toe-hold nucleic acid sequence complementary to the fourth nucleic acid sequence.

Having described various embodiments, it is believed that the invention will become even more apparent by reference to the following examples. It will be appreciated that the examples are presented solely for the purpose of illustration and should not be construed as limiting the invention. For instance, although the experiments described below may be carried out in laboratory or pilot plant setting, one skilled in the art could adjust specific numbers, dimensions and quantities up to appropriate values for a full scale plant.

EXPERIMENTS

Experiments were conducted to examine: 1) the preparation of a polyacrylamide gel crossed linked via a nucleic acid sequence according to the present invention and the ability to prevent cross-linking with an oligomer comprising a nucleic acid sequence added to the gel; and 2) the different mechanical properties of the nucleic acid cross-linked gel.

Experiment 1

The nucleic acid sequences were DNA strands designated as SA1, SA2, L1, and R1, the specific sequences as defined below:
SA1: 5' Phosphoramidite-AGTACGGACACTAGCTG-GATCTGAGGATTAGT (SEQ ID NO.: 1)
SA2: 5' Phosphoramidite-ATTCATACCCTTAGTATCGCA-CACACCTACTT (SEQ ID NO.: 2)
L1: 5' ACTAATCCTCAGATCCAGCTAAGTAGGT-GTGTGCGATACTTTACATTGAT (SEQ ID NO.: 3)
R1: 5' ATCAATGTAAAGTATCGCACACAC-CTACTTAGCTGGATCTGAGGATTAGT (SEQ ID NO.: 4)

Through their functionalization with a phosphoramidite (e.g., Product AC-350 from Apogent Discoveries, Hudson NH), SA1 and SA2 can be incorporated into polyacrylamide. The linking strand "L1" hybridizes with both SA1 and SA2 and serves to crosslink the gel. The removal strand "R1" is complementary to the L1 strand, and was used to test the ability to prevent the re-association of SA1, SA2 and L1, as further described below. All DNA strands were purchased in High Performance Liquid Chromatography or Polyacrylamide Gel Electrophoresis purified grades from Operon Technologies, Inc. (now QIAGEN Operon, Inc., Alameda, CA) or Integrated DNA Technologies (Coralville, IA).

SA1 and SA2 were separately polymerized with acrylamide. Separate stock solutions of SA1 and SA2 were prepared at a concentration of 1 mM in TE buffer (10 mM Tris, 1 mM EDTA, pH 8.0). A five mL solution comprising 40% acrylamide monomer in $H_2O$, 30 ml of SA1 stock solution, 10 ml of $H_2O$, and 5 ml of 10X TBE buffer (a 10 times concentrate of 89 mM Tris-borate, 2.5 mM EDTA, pH 8.3 at 20° C.) was mixed together. Dry nitrogen was bubbled through the mixture for 5 min. An initiator solution consisting of 0.5 ml $H_2O$, 0.05 g ammonium persulfate and 25 ml N,N,N',N'-Tetramethylethylenediamine (TEMED) was prepared shortly before use (less than about 6 hours). About 0.7 ml of this solution was added to the SA1 mixture. Nitrogen was bubbled through the mixture for another 20 minutes as polymerization took place and the fluid became viscous. An SA2 mixture was similarly prepared. The SA1 and SA2 solutions were then mixed together and water was added to account for evaporative loss by bringing the total volume of the fluid to 100 ml. To one 33 ml portion of this solution, designated as the cross-inked mixture, 10 ml of L1 stock solution was added. To another 33 ml portion of this solution, designated as the control solution, 10 ml of TE buffer was added.

A ~1 mm diameter sapphire sphere was used to measure the viscosity of the fluids by monitoring the rate at which the sapphire sphere moved through the fluid under the force of gravity for a period of time (from about 1.5 s to about 105 s) at progressively increasing temperatures ranging from about 20° C. to about 60° C. For example, at room temperature, in the control mixture, the sphere sank at a rate of ~0.1 cm/sec. In contrast, in the cross-linked mixture, no movement of the sphere was detectable, indicating that the velocity was less than about $3 \times 10^{-5}$ cm/sec.

The measured velocities for the sapphire sphere were converted into viscosities using Stokes law:

$$F = m \cdot g = \pi \cdot \eta \cdot r \cdot v \tag{1}$$

where m is the boyant mass of the sphere (gm), g the acceleration due to gravity ($cm/s^2$) $\eta$ the viscosity (Poise), r the diameter of the sphere (cm), and v is the velocity with which the sphere moves through the fluid (cm/s). Given that the density of sapphire is 3.965 $g/cm^3$, the viscosity in poise is given by:

$$\eta = 1.6 \cdot (g/s^2) \cdot (1/v) \tag{2}$$

Figure 6:
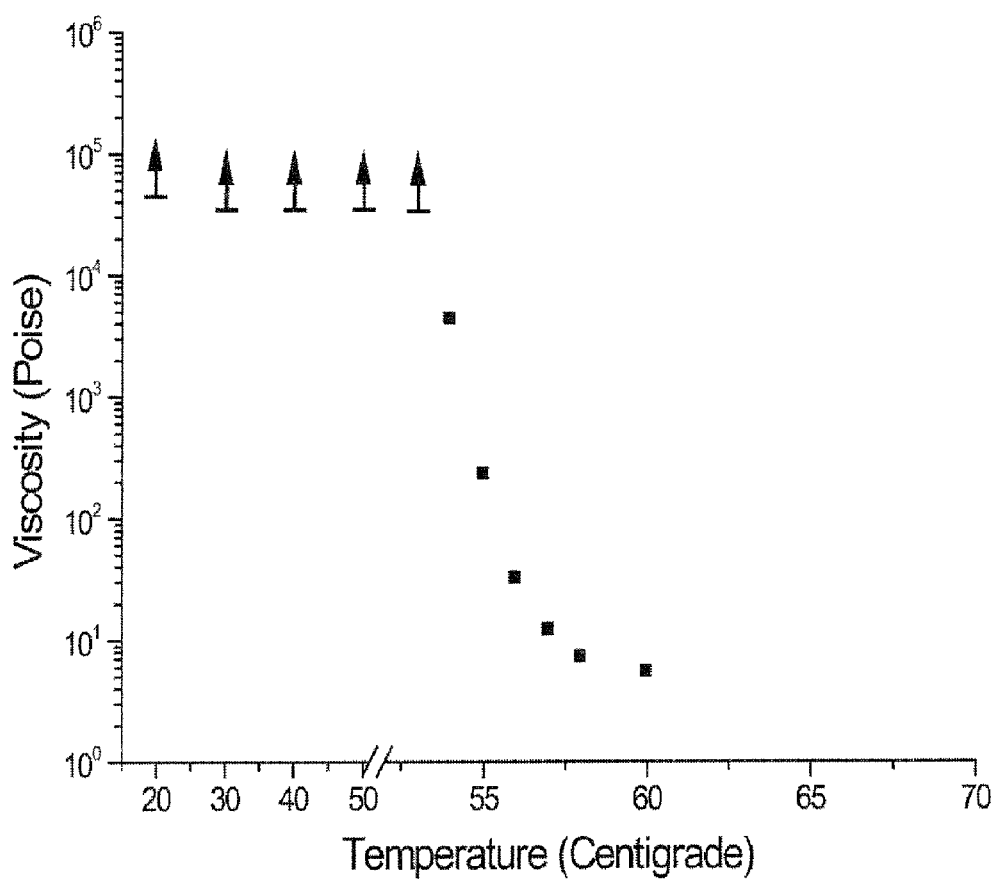
FIG. 6 illustrates the relationship between temperature and viscosity for a representative composition of the present invention.

As illustrated in FIG. 6, below about 54° C., the cross-linked mixture exhibited no detectable flow, and behaved like a gel. Hence, the bars with upward arrows in FIG. 6 indicate lower bounds. For comparison, the viscosity of water at ~20° C. equals about $1 \times 10^{-2}$ Poise. When the cross-linked mixture was heated above the expected melting temperature of DNA (defined as the temperature at which half of the double strands are dissociated), the gel became fluid and the viscosity decreased.

After performing the melting study, the removal strand R1 was added to the cross-linked mixture at ~55° C. and the solution was mixed for about 8 minutes. The resulting solution was then cooled to ~20° C. and viscosity measurements were repeated, by monitoring the rate at which the sapphire sphere moved through the fluid, as described above. A viscosity of about 7 Poise was determined, as compared to the lower bound of viscosity of about 54,000 Poise measured in the original cross-linked mixture (see FIG. 5). This demonstrates that the R1 strand was capable of preventing cross-link foiniation.

Experiment 2

The viscosity of gel compositions of the present invention were examined at different degrees of cross-link density and as a function of temperature. In addition, the elastic modulus of certain gel compositions were measured.

Two DNA strands designated SA3 and SA4 comprised of random DNA sequences and 20 bases in length were functionalized at the 5' end with a phosphoramidite. Sections complementary to SA1 and SA2 were each incorporated into a cross-linker strand L2 of 50 bases. The additional 10 bases, designated as a toe-hold nucleic acid sequence, served as a point of attachment at which a removal strand R2 attaches to L2 thereby promoting dissociation of the cross-link. The specific sequences are as defined below:

SA3: 5' Phosphoramidite-TATGCACACTGAGTCTGACG (SEQ ID NO.: 5)
SA4: 5' Phosphoramidite-ATAGCGAGCGTCACGTATCT (SEQ ID NO.: 6)
L2: 5'CGTCAGACTCAGTGTGCATAAGATACGTGACGCTCGCTAT (SEQ ID NO.: 7)
R2: 5'ATAGCGAGCGTCACGTATcTTATGCACACTGAGTCTGACG (SEQ ID NO.: 8)

SA3 and SA4 were separately incorporated into polyacrylamide, similar to that described in Experiment 1, and then mixed to form 26 µL of a pre-gel mixture comprising: ~0.43 wt % SA3; ~0.42 wt % SA4; and ~3 wt % acrylamide in TBE buffer. A ~0.79 mm diameter sapphire bead was placed in the pre-gel mixture, the container holding the mixture and bead was sealed, and then the container was placed in a temperature-controlled water bath. Next, a series of viscosity measurements as a function of temperature from ~27 to ~85° C. were made, similar to that described in Experiment 1. The container was then removed from the bath, and a volume of L2 was added to the mixture to form a gel composition comprising ~0.06 wt % L2. This amount equals ~5.6% of the stoichiometric amount for complete hybridization to the SA3 and SA4 strands (i.e., ~5.6:100:100 of L2:SA3:SA4). Water was evaporated off from the mixture to provide substantially the same volume as the pre-gel mixture. The container was then resealed, returned to the water bath, and another series of viscosity measurements as a function of temperature were made. This process was repeated several times with step-wise additions of L2 to the gel composition, until a ~100:100:100 stoichiometry of L2:SA3:SA4 was attained (~1 wt % L2).

Figure 7:
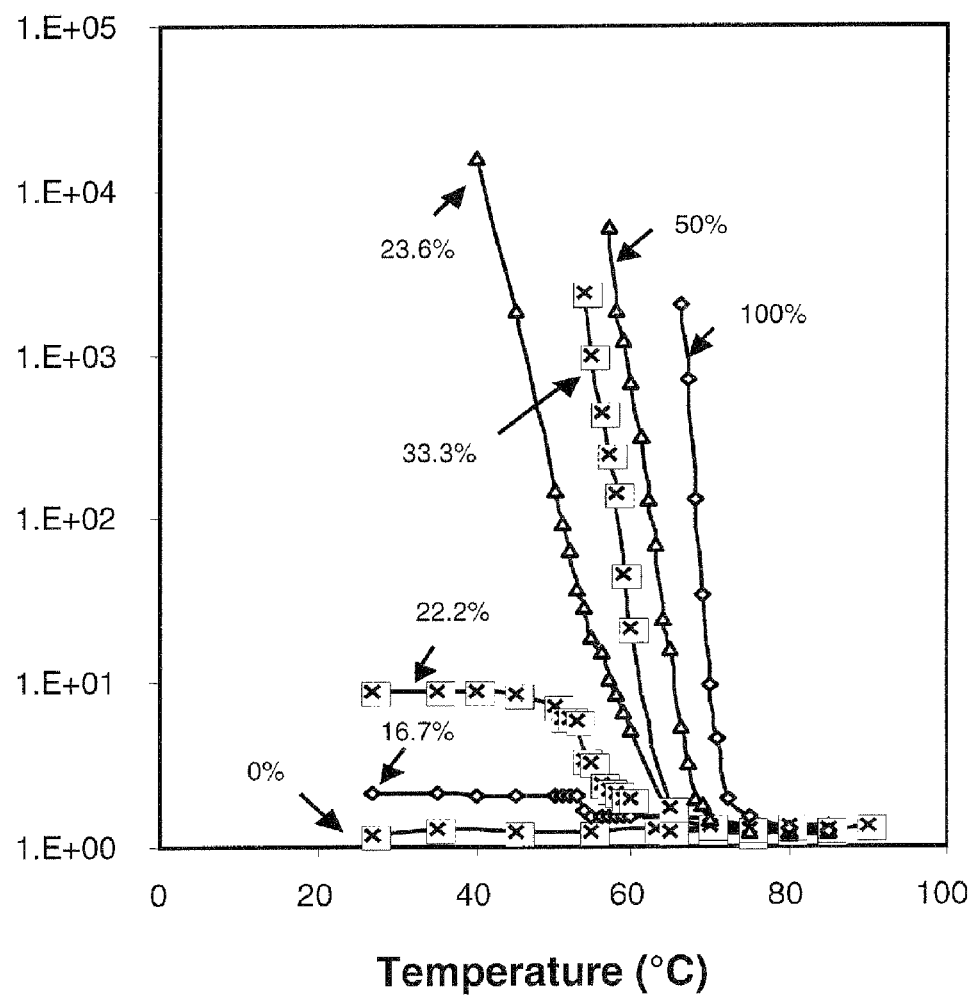
FIG. 7 illustrates the relationship between temperature and viscosity for representative compositions of the present invention having different amounts of a nucleic acid sequence serving as a cross-linker.

Selected results from these measurements are depicted in FIG. 7. The results in FIG. 7 illustrate that in the absence of cross-linker L2, the viscosity was substantially constant from ~27 to ~85° C. In contrast, as L2 was added, viscosity at ~27° C. increased as a nonlinear function of the amount of cross-linker L2 present. In particular, there was a large increase in the viscosity when the amount of L2 increased from ~22.2% to ~23.6% of the stoichiometric amount for complete hybridization. Thus, for this particular combination of SA3, SA4, and L2, a cross-linker concentration of at least about 23% of the stoichiometric amount of L2 is preferred to facilitate optimal gel formation. For gels containing ~23.6% of the stoichiometric amount of L2 and higher, the viscosity decreased in a nonlinear fashion with respect to increasing temperature.

Figure 8:
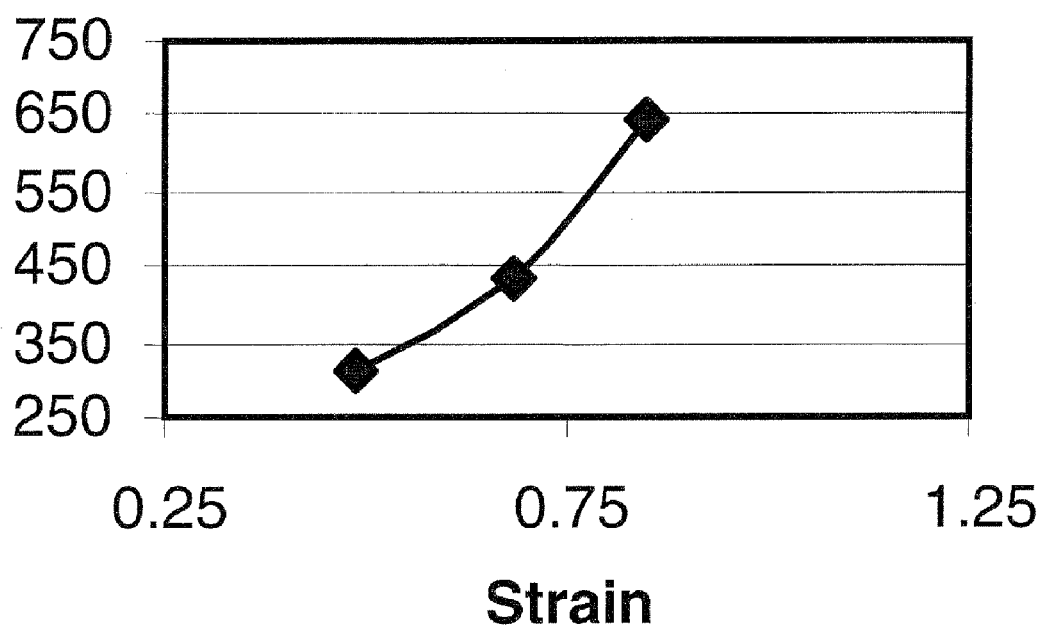
FIG. 8 illustrate the stress-strain relationship for a representative composition of the present invention.

Another series of experiments were conducted using these same DNA strands to measure the elastic modulus of particular gel compositions. For example, one such gel composition comprising: ~0.14 wt % SA3; ~0.14 wt % SA4; 0.34 wt % L2; and ~3 wt % acrylamide, corresponding to ~33.3% of the stoichiometric amount for complete hybridization. The elastic modulus was measured by affixing a thin, small loading surface fashioned from a microscopic slide cover slip to the top of the cylindrical sample. The surface was loaded with the tips of brass pins of various weights. Deflections were measured by focusing on the loading surface with an inverted microscope. Representative data of the stress-strain curve are illustrated in FIG. 8. The linear elastic modulus was determined from a curve fit to data such as that shown in FIG. 8. The linear elastic modulus is the elastic modules at zero strain. This was determined by extrapolating from the data points to zero strain. Since the data points depicted in FIG. 8 do not lie on a straight line a curve fit has to be performed and extended to zero strain.

The same gel composition was used to demonstrate the ability of the removal strand, R2, to facilitate the dissociation of SA3, SA4 and L2, and thereby convert the gel back to a fluid state. Micron-sized fluorescent beads were added to SA3 and SA4 before the addition of L2. The resulting gel after the addition of L2 was cut into several 0.2 mm² pieces. One such piece was immersed in a Well containing a 20 mL volume of a 1 mM solution of R2. Another piece of the gel, serving as a control was immersed in a Well containing 20 mL of TE buffer solution. The fluorescent beads served to increase the visibility of the gel, and allowed changes in size to be monitored as the gel dissolves and the beads become dispersed throughout the fluid volume. Photographs of both Wells were taken over regular intervals to monitor the rate of dissociation of the cross-linked gels. The dissociation of the cross-linked gel in the presence of the R2 strand occurred within ~4 minutes as indicated by substantially complete dispersal of the fluorescent beads throughout the liquid contained in the first well. In comparison, the fluorescent beads in the second Well remained trapped in the gel for at least ~24 hours, at which time the experiment was terminated.

Figure 9:
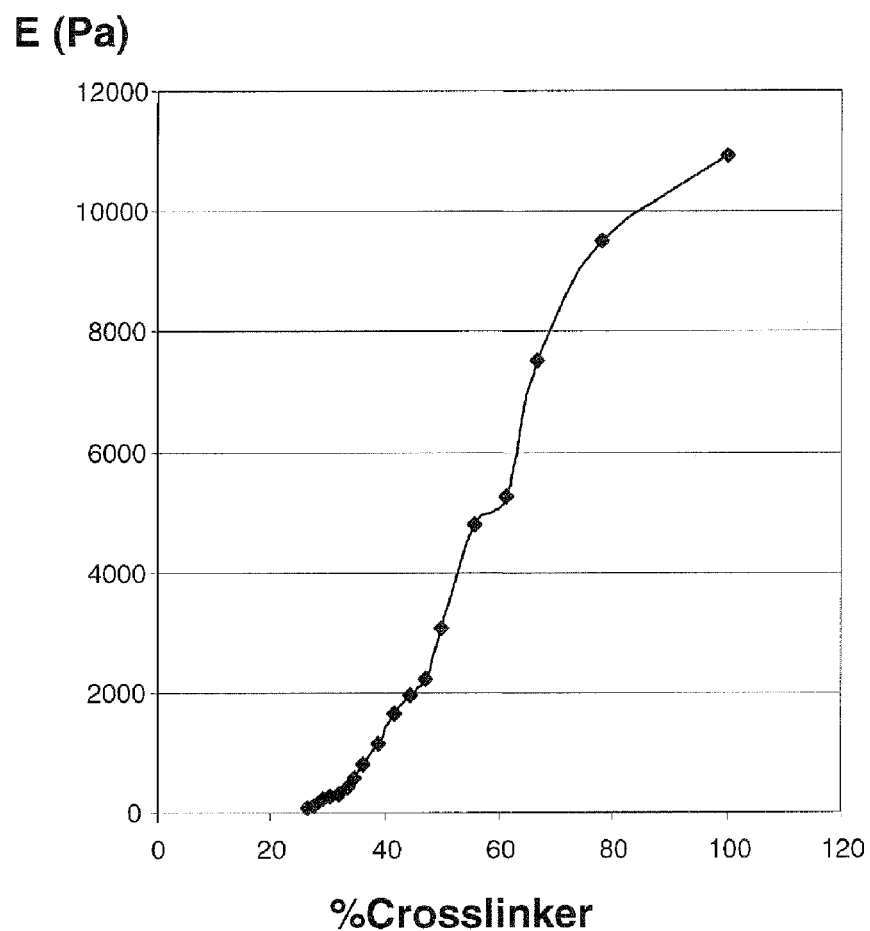
FIG. 9 illustrates the change in elastic modulus for representative compositions of the present invention having different amounts of a linking nucleic acid sequence.

The change in elastic modulus (E) of polyacrylamide gels, comprising 3 wt % acrylamide and with sidechains of SA1 and SA2, as a function of various amounts of the cross-linking L1 strand is shown in FIG. 9. A four order of magnitude increase in elastic modulus occurs as the amount of L1 increases from about 25 to about 80 percent.

Although the present invention has been described in detail, those of ordinary skill in the art should understand that they can make various changes, substitutions and alterations herein without departing from the scope of the invention.

What is claimed is:

1. A modified or isolated composition, comprising:
a gel formed from:
first polymers having first functional groups comprising a first nucleic acid sequence attached as side-chains thereto; and
second polymers having second functional groups comprising a second nucleic acid sequence attached as side-chains thereto, said first and said second functional groups form reversible cross-links between said first and said second polymers, wherein said cross links comprise a plurality of hydrogen bonds between complementary base portions of said first and said second nucleic acid sequences; and
further including therein said gel an active agent disposed between said first and second polymers, said active agent capable of being released by an interaction of a substance with said first or said second nucleic acid sequences to thereby break said cross-links, wherein:
said first and second polymers are separate polymers and said first and second polymers are held together by said hydrogen bonds,
said gel is in a solid state when said cross-links are unbroken, and
said gel is in a fluid state when said cross-links are broken.

2. The composition as recited in claim 1, wherein said substance is an enzyme capable of breaking said cross-links by a cleavage of said first and said second nucleic acid sequences.

3. The composition as recited in claim 2, wherein said enzyme is selected from the group consisting of nucleases and ribozymes.

4. The composition as recited in claim 3, wherein said nuclease is a exodeoxyribonuclease, exoribonuclease, endodeoxyribonuclease, or endoribonuclease as classified according International Union of Biochemistry and Molecular Biology enzyme nomenclature categories EC 3.1.11 to EC 3.1.31.

5. The composition as recited in claim 1, wherein said substance comprises a third nucleic acid sequence and at least one of said first nucleic acid sequence or said second nucleic acid sequence further comprise a nucleic acid sequence, wherein said third nucleic acid sequence is sufficiently complementary to a portion of said nucleic acid sequence such that said third nucleic acid sequence causes a dissociation of said cross-links.

6. The composition as recited in claim 1, further includes a third nucleic acid sequence capable of attaching to said first and said second nucleic acid sequences to facilitate formation of said cross-links.

7. The composition as recited in claim 6, wherein said substance is an enzyme capable of breaking said cross-links by a cleavage of said third nucleic acid sequence.

8. The composition as recited in claim 6, wherein said substance is a fourth nucleic acid sequence and said third nucleic acid sequence comprises a nucleic acid sequence, wherein said fourth nucleic acid sequence is sufficiently complementary to said nucleic acid sequence to cause a dissociation of said cross-links.

9. The composition as recited in claim 1 wherein said active agent is selected from the group consisting of:
a protein; and
a nucleic acid sequence.

10. The composition as recited in claim 1, wherein said active agent comprises a nucleic acid sequence.

11. The composition as recited in claim 6, wherein said active agent comprises a nucleic acid sequence released from said first or said second nucleic acid sequence.

12. The composition as recited in claim 1, wherein said active agent comprises drugs.

13. The composition as recited in claim 1, wherein said active agent comprises antibiotics.

* * * * *

SEQUENCE LISTING

<160> NUMBER OF SEQ ID NOS: 8

<210> SEQ ID NO 1
<211> LENGTH: 32
<212> TYPE: DNA
<213> ORGANISM: Artificial sequence
<220> FEATURE:
<223> OTHER INFORMATION: a phosphoramidite modified oligonucleotide that
      serves as a cross-linking agent for a polyacrylamide gel

```
<400> SEQUENCE: 1
agtacggaca ctagctggat ctgaggatta gt                                       32

<210> SEQ ID NO 2
<211> LENGTH: 32
<212> TYPE: DNA
<213> ORGANISM: Artificial sequence
<220> FEATURE:
<223> OTHER INFORMATION: a phosphoramidite modified oligonucleotide that
      serves as a cross-linking agent for a polyacrylamide gel

<400> SEQUENCE: 2
attcataccc ttagtatcgc acacacctac tt                                       32

<210> SEQ ID NO 3
<211> LENGTH: 50
<212> TYPE: DNA
<213> ORGANISM: Artificial sequence
<220> FEATURE:
<223> OTHER INFORMATION: a oligonucleotide that serves as a
      cross-linking agent for a polyacrylamide gel

<400> SEQUENCE: 3
actaatcctc agatccagct aagtaggtgt gtgcgatact ttacattgat                    50

<210> SEQ ID NO 4
<211> LENGTH: 50
<212> TYPE: DNA
<213> ORGANISM: Artificial sequence
<220> FEATURE:
<223> OTHER INFORMATION: Description of Artifical Sequence:  a
      oligonucleotide that serves as a removal agent for a cross-linked
      polyacrylamide gel

<400> SEQUENCE: 4
atcaatgtaa agtatcgcac acacctactt agctggatct gaggattagt                    50

<210> SEQ ID NO 5
<211> LENGTH: 22
<212> TYPE: DNA
<213> ORGANISM: Artificial sequence
<220> FEATURE:
<223> OTHER INFORMATION: Description of Artifical Sequence:  a
      phosphoramidite modified oligonucleotide that serves as a
      cross-linking agent for a polyacrylamide gel

<400> SEQUENCE: 5 tatgcacacact gagtctgacg                                                   22

<210> SEQ ID NO 6
<211> LENGTH: 20
<212> TYPE: DNA
<213> ORGANISM: Artificial sequence
<220> FEATURE:
<223> OTHER INFORMATION: a phosphoramidite modified oligonucleotide that
      serves as a cross-linking agent for a polyacrylamide gel

<400> SEQUENCE: 6
atagcgagcg tcacgtatct                                                     20

<210> SEQ ID NO 7
<211> LENGTH: 40
<212> TYPE: DNA
<213> ORGANISM: Artificial sequence
<220> FEATURE:
<223> OTHER INFORMATION: a oligonucleotide that serves as a
      cross-linking agent for a polyacrylamide gel
```

```
<400> SEQUENCE: 7
cgtcagactc agtgtgcata agatacgtga cgctcgctat                    40

<210> SEQ ID NO 8
<211> LENGTH: 40
<212> TYPE: DNA
<213> ORGANISM: Artificial sequence
<220> FEATURE:
<223> OTHER INFORMATION: a oligonucleotide that serves as a removal
      agent for a cross-linked polyacrylamide gel

<400> SEQUENCE: 8
atagcgagcg tcacgtatct tatgcacact gagtctgacg                    40
```